United States Patent [19]

Reap

[11] Patent Number: 4,576,633

[45] Date of Patent: Mar. 18, 1986

[54] HERBICIDAL SULFONAMIDES

[75] Inventor: James J. Reap, Wilmington, Del.

[73] Assignee: E. I. Du Pont de Nemours and Company, Wilmington, Del.

[21] Appl. No.: 697,375

[22] Filed: Feb. 1, 1985

Related U.S. Application Data

[62] Division of Ser. No. 477,969, Mar. 23, 1983, Pat. No. 4,515,624.

[51] Int. Cl.⁴ .................. C07D 25/18; C07D 401/12; A01N 43/70; A01N 43/68

[52] U.S. Cl. ..................................... 71/93; 544/206; 544/208; 544/211; 544/212; 544/207; 544/209; 544/113

[58] Field of Search ............... 544/206, 208, 211, 212, 544/207, 209, 113; 71/93

[56] References Cited

U.S. PATENT DOCUMENTS 4,435,205  3/1984  Reap ................................. 544/212
4,534,789  8/1985  Reap ................................. 544/206

Primary Examiner—John M. Ford

[57] ABSTRACT

Certain sulfonylurea compounds with oxysulfonyl-, thiosulfonyl- or aminosulfonyl-containing groups are useful as pre- and/or post-emergence herbicides.

17 Claims, No Drawings

HERBICIDAL SULFONAMIDES

This is a division of application Ser. No. 477,969 filed Mar. 23, 1983 now U.S. Pat. No. 4,515,624.

Background of the Invention

The present invention relates to herbicidal sulfonamides, and, more particularly, to ortho-oxysulfonyl-, thiosulfonyl- or aminosulfonyl-sulfonylurea compounds which are useful as pre- and/or post-emergence general and selective herbicides.

U.S. Pat. No. 4,169,719 discloses and claims N-(heterocyclicaminocarbonyl)arylsulfonamides of the formula:

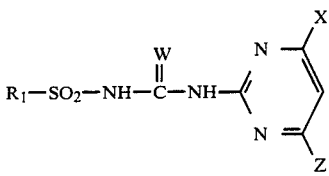

wherein
R₁ can be

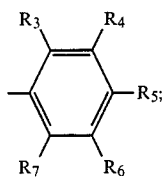

W can be O or S;
R₃, R₄, R₅, R₆ and R₇ can be H, alkyl, halo or alkoxy, as more specifically defined therein; and
X and Z can be various substituents including H, methyl and methoxy.

These compounds are useful as plant growth regulants and as herbicides.

The following references disclose other herbicidal sulfonamides of similar, though patentably distinct, structures.

U.S. Pat. No. 4,127,405 discloses and claims N-(1,3,5-triazin-2-ylaminocarbonyl)arylsulfonamides, which are also plant growth regulants and herbicides.

U.S. application Ser. No. 340,301 now U.S. Pat. No. 4,425,153, discloses compounds such as ortho-(acyloxy)benzenesulfonamides which are useful as herbicides.

U.S. application Ser. No. 261,751 now U.S. Pat. No. 4,394,153, (EPO Publication No. 44,213) discloses herbicidal sulfamatesulfonylureas of the formula

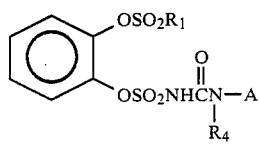

wherein R₁ can be C₁–C₄ alkyl or C₁–C₄ alkyl substituted with 1-3 atoms of F, Cl or Br.

U.S. application Ser. No. 262,813 now abandoned (EPO Publication No. 44,212) discloses methylsulfonatesulfonylureas of the general formula

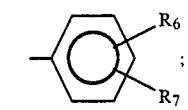

where
W can be O or S;
Q is O or NR₅;
R₁ is C₁–C₄ alkyl, C₁–C₄ alkyl substituted with 1-3 atoms of F, Cl or Br, CH₂CH₂OCH₃, CH₂CH₂CH₂OCH₃ or

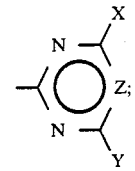

R₂ is H, F, Cl, Br, OCH₃, NO₂, CF₃ or C₁–C₂ alkyl;
R₃ is H, F, Cl, Br or CH₃;
R₄ is H, CH₃ or OCH₃;
R₅ is C₁–C₄ alkyl;
R₆ and R₇ are independently H, F, Cl, Br, CH₃, CF₃, NO₂ or OCH₃;
A can be, among other values,

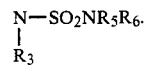

X is NH₂, N(CH₃)₂, NHCH₃, C₁–C₄ alkyl, C₁–C₄ alkyl substituted with 1-3 atoms of F, Cl or Br, CH₂OCH₃, CH₂OCH₂CH₃, C₁–C₄ alkoxy, C₁–C₂ alkylthio, C₃–C₄ alkenyloxy, C₃–C₄ alkynyloxy, OCH₂CH₂OCH₃ or C₂–C₄ alkoxy substituted with 1-3 atoms of F, Cl or Br;
n is 1 or 2;
Y is H, CH₃, OCH₃ or Cl;
X₁ is O or CH₂;
Y₁ is H, CH₃, OCH₃ or Cl;
X₂ and Y₂ are independently CH₃ or OCH₃; and
Z can be CH, N, CCH₃, CBr, CCl, CF, CI, CC₂H₅, CCH₂CH₂Cl or CCH₂CH=CH₂.

The compounds of the present invention differ from the structures taught by the prior art because of an ortho-sulfamoyloxy moiety OSO₂NR₅R₆, an ortho-thio-sulfonate moiety SSO₂L, or an ortho-aminosulfonyl amino moiety $$\underset{R_3}{\overset{|}{N}}-SO_2NR_5R_6.$$

SUMMARY OF THE INVENTION

This invention relates to compounds of Formula I, to agriculturally suitable compositions containing them and to their use as general or selective pre-emergent or post-emergent herbicides.

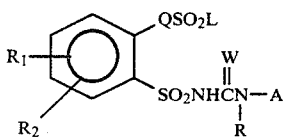

wherein
W is O or S;
R is H or CH₃;
Q is O, S or NR₃;
L is R₄, NR₅R₆ or N(OCH₃)CH₃;
R₁ is H, F, Cl, Br, CH₃, OCH₃, CF₃ or NO₂;
R₂ is H or Cl;
R₃ is H or C₁-C₃ alkyl;
R₄ is C₁-C₄ alkyl, C₁-C₄ alkyl substituted with 1-3 atoms of F, Cl or Br, CH₂CH₂OCH₃, CH₂CH₂CH₂OCH₃ or

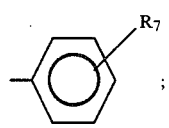

R₅ and R₆ are independently C₁-C₃ alkyl, or R₅ and R₆ may be taken together to be —(CH₂)₄—, —(CH₂)₅— or —(CH₂)₂O(CH₂)₂—;
R₇ is H, F, Cl, Br, CH₃, CF₃, NO₂ or OCH₃;
A is

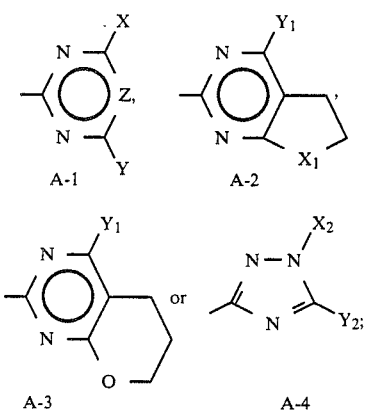

X is CH₃, OCH₃, Cl, CH₂CH₃, OCH₂CH₃ or OCF₂H;
Y is H, NH₂, NHCH₃, N(CH₃)₂, C₁-C₄ alkyl, C₁-C₄ alkyl substituted with 1-3 atoms of (a), F, (b) Cl or (c) Br, CH₂OCH₃, CH₂OCH₂CH₃, C₁-C₄ alkoxy, C₁-C₂ alkylthio, C₃-C₄ alkenyloxy, C₃-C₄ alkynyloxy, OCH₂CH₂OCH₃, CH(OCH₃)₂, CH(OCH₂CH₃)₂,

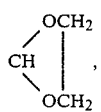

OCH₂CF₃, OCH₂CH₂F, OCH₂CH₂Cl, OCH₂CH₂Br or GCF₂T wherein G is O or S and T is H, CHClF, CHBrF, CF₂H or CHFCF₃;
Z is CH, N, CCH₃, CBr, CCl, CF or CCH₂CH₃,
X₁ is O or CH₂;

Y₁ is H, CH₃, OCH₃ or Cl;
X₂ is CH₃, CH₂CH₃ or CH₂CF₃;
Y₂ is CH₃, OCH₃ or SCH₃;
provided that
(1) when Q is O or NR₃, then L is NR₅R₆ or N(OCH₃)CH₃;
(2) when X is Cl, then Z is CH and Y is NH₂, NHCH₃, N(CH₃)₂, CH₃, OCH₃ or OCF₂H;
(3) when W is S, then R is H;
and their agriculturally suitable salts.

Preferred for their higher herbicidal activity and/or more favorable ease of synthesis are:
(1) Compounds of Formula I where W is O;
(2) Compounds of preferred 1 where R₂ is H;
(3) Compounds of preferred 2 where R₄ is C₁-C₄ alkyl, R₃ is CH₃, L is N(OCH₃)CH₃ or NR₅R₆, R₅ is CH₃ and R₆ is CH₃ or CH₂CH₃;
(4) Compounds of preferred 3 where Q is O and R₁ is H, CH₃ or Cl;
(5) Compounds of preferred 4 where A is A-1, Z is CH or N, X is CH₃, OCH₃, Cl or OCF₂H and Y is CH₃, CH₂CH₃, OCH₃, OCH₂CH₃, OCF₂H, SCF₂H, CH₂OCH₃ or CF₃; and
(6) Compounds of preferred 5 where R is H and R₁ is H.

Specifically preferred for their highest herbicidal activity and/or more favorable ease of synthesis are:
N-[(4,6-dimethoxypyrimidin-2-yl)aminocarbonyl]-2-(dimethylaminosulfonyloxy)benzenesulfonamide;
N-[(4-methyl-6-methoxypyrimidin-2-yl)aminocarbonyl]-2-(dimethylaminosulfonyloxy)benzenesulfonamide;
N-[(4,6-dimethylpyrimidin-2-yl)aminocarbonyl]-2-(dimethylaminosulfonyloxy)benzenesulfonamide;
N-[(4-methyl-6-methoxy-1,3,5-triazin-2-yl)aminocarbonyl]-2-(dimethylaminosulfonyloxy)benzenesulfonamide;
N-[(4,6-dimethoxy-1,3,5-triazin-2-yl)aminocarbonyl]-2-(dimethylaminosulfonyloxy)benzenesulfonamide; and
N-[(4-chloro-6-methoxypyrimidin-2-yl)aminocarbonyl]-2-(dimethylaminosulfonyloxy)benzenesulfonamide.

This invention also relates to agriculturally suitable salts of compounds of Formula I.

SYNTHESIS

The compounds of this invention can be made as outlined below. The compounds of Formula (IV), (VI), (VIII) or (X) can be prepared by reacting an appropriate 2-aminopyrimidine, 2-aminotriazine, 2-aminobicyclopyrimidine or 2-aminotriazole of Formula (III), (V), (VII) or (IX) with an appropriately substituted sulfonylisocyanate or isothiocyanate, of Formula (II), where Q, L, R, R₁, R₂, X, Y, Z, X₁, X₂, Y₁, Y₂ and W are as previously defined.

The reaction is best carried out in inert solvents such as methylene chloride and acetonitrile. The mode of addition is not critical, however, it is often convenient to add a solution of the isocyanate or isothiocyanate of Formula (II) to a stirred suspension of the aminoheterocycle (III), (V), (VII) or (IX).

The reaction is generally exothermic. In some cases, the desired product is insoluble in the reaction medium and crystallizes from it in pure form. Products soluble in the reaction medium are isolated by evaporation of the solvent and trituration of the residue with solvents such as diethyl ether, 1-chlorobutane, or hexanes and filtration.

(1.)
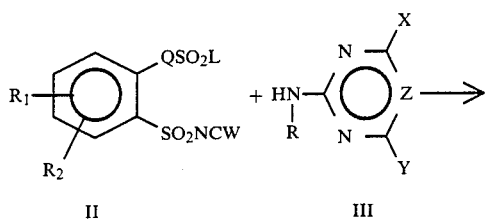

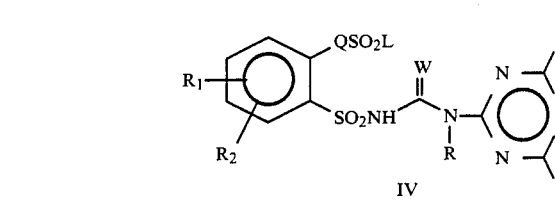

(2.)
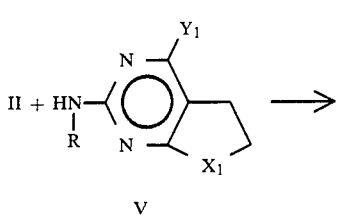

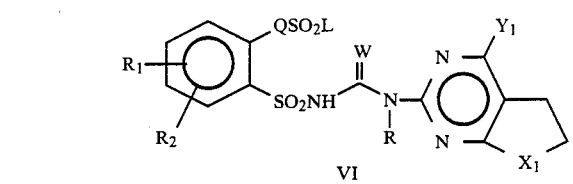

(3.)
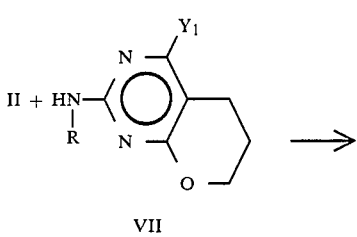

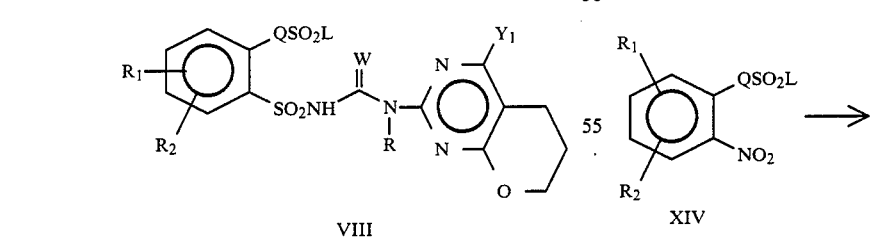

(4.)
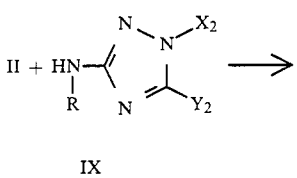

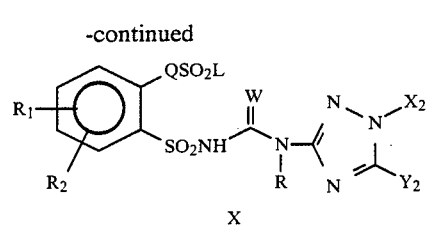

Compounds of Formula XIII may also be prepared by the procedure of Equation 5 wherein R, $R_1$, $R_2$, Q, L and A are as previously defined.

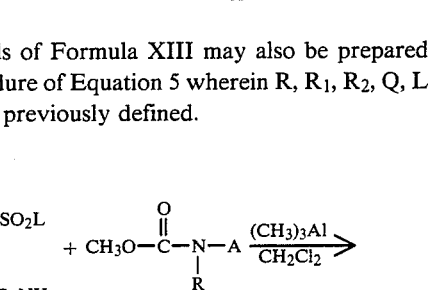

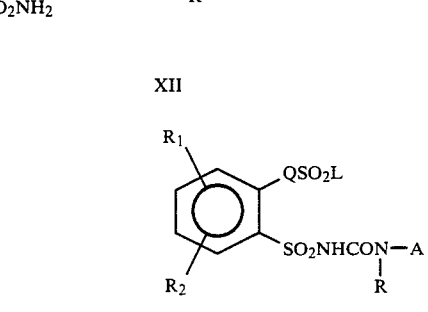
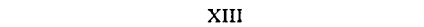

The reaction of Equation 5 is best carried out in methylene chloride at 25° to 40° C. for 24 to 96 hours under a nitrogen atmosphere. The product can be isolated by the addition of an aqueous acetic acid solution followed by extraction of the product into methylene chloride or direct filtration of a product of low solubility. The product can ordinarily be purified by trituration with solvents such as n-butyl chloride or ether or by column chromatography.

Further details of this reaction and the preparation of the carbamates of Formula XII can be found in unexamined European Patent Application 174-73.

Sulfonamides of Formula XI and XVIII can be prepared as shown by Equations 6 and 7.

(6.)
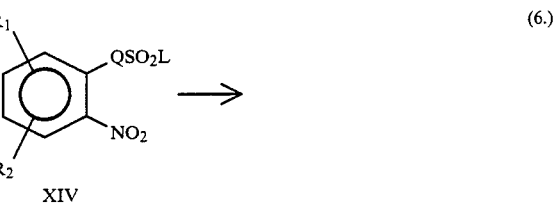

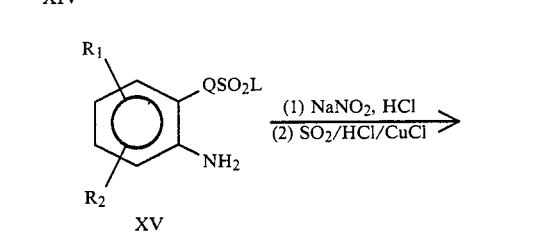

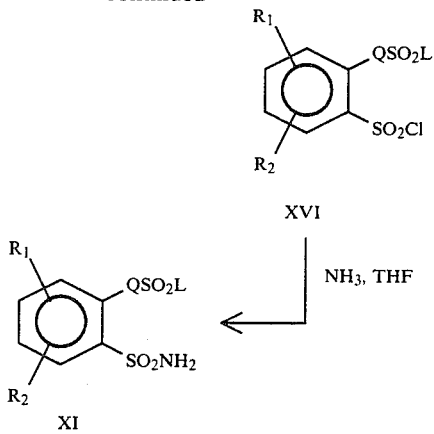

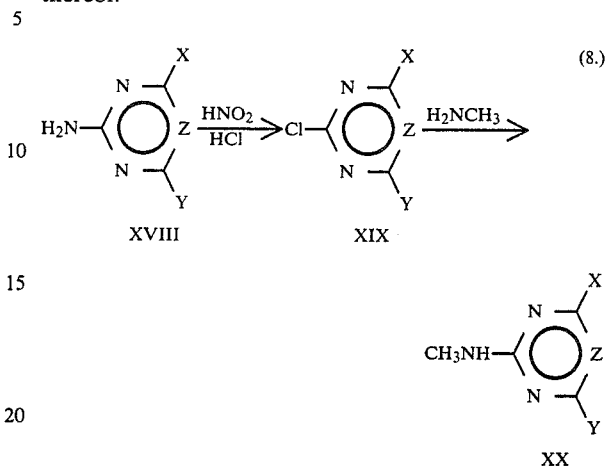

The reduction of the nitro compounds such as XIV to anilines XV is achieved by procedures well known to those skilled in the art.

Anilines of Formula XV are converted to sulfonyl chlorides by well known procedures. For further details, see H. L. Yale and F. Sowinski, *J. Org. Chem.*, 25, 1824 (1960).

Sulfonamides of Formula XI are obtained by treatment of sulfonyl chlorides of Formula XVI with NH$_3$ by procedures known to those skilled in the art.

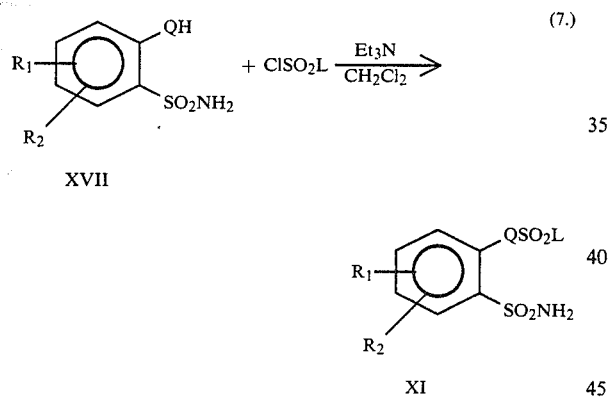

The reaction of Equation 7 is carried out in methylene chloride at 0°–40° C. for 24–72 hours. The product can be isolated by washing the methylene chloride reaction mixture with water followed by dilute aqueous HCl, drying the organic phase, filtering and evaporating the solvent.

Compounds of Formula XVII may be prepared by the process described in patent application U.S. Ser. No. 377,370, filed May 12, 1982.

Sulfonamides of Formula XI may conveniently be converted to the corresponding isocyanates or isothiocyanates of Formula II by methods described in U.S. Pat. No. 4,127,405.

The synthesis of the heterocyclicamine derivatives has been reviewed in "The Chemistry of Heterocyclic Compounds", a series published in Interscience Publ., New York and London.

2-Aminopyrimidines are described by D. J. Brown in "The Pyrimidines", Vol. XVI of the above series which are herein incorporated by reference.

The preparation of aminobicyclopyrimidines are described in unexamined European Patent No. 15683.

The aminoheterocyclic intermediates of Formula III, V, VII or IX in which R is CH$_3$, may be prepared by the following procedure, or by appropriate modifications thereof.

A solution of the amine XVIII in concentrated hydrochloric acid is contacted with an aqueous sodium nitrite solution and the chloro compound XIX is isolated by filtration of the acidic solution (see for example, Bee and Rose, *J. Chem. Soc. C.*, 2051 (1966) for the case in which Z is CH and X and Y are OCH$_3$). Displacement of the chlorine may be accomplished by heating with an excess of methylamine in water to obtain the methylaminoheterocycle XX.

The preparation of 2-aminotriazoles of Formula IX are described in U.S. Ser. No. 382,711, filed May 28, 1982, now U.S. Pat. No. 4,421,550.

The compounds of this invention and their preparation are further illustrated by the following examples, wherein temperatures are given in degrees Centigrade and parts are by weight unless otherwise indicated.

EXAMPLE 1

2-(Dimethylaminosulfonyloxy)benzenesulfonyl isocyanate

To 6.0 g (0.021 mole) 2-(dimethylaminosulfonyloxy)-benzenesulfonamide suspended in 75 ml dry xylenes was added 2.1 g (0.021 mole) N-butyl isocyanate and a catalytic amount of 1,4-diazobicyclo[2.2.2]octane (~0.05 g). This mixture was rapidly heated to reflux temperature (~135° C.) and 3.0 ml of phosgene was slowly added (at such a rate as to keep the reaction temperature greater than 128° C.). The phosgene addition required ~3 hours. The reaction was cooled to room temperature, filtered under N$_2$, and the solvent evaporated under reduced pressure. The infrared spectrum of the resultant oil was consistent for 2-(dimethylaminosulfonyloxy)benzenesulfonyl isocyanate, (2240 cm$^{-1}$).

EXAMPLE 2

N-[(4,6-Dimethoxypyrimidin-2-yl)aminocarbonyl]-2-(dimethylaminosulfonyloxy)benzenesulfonamide To a suspension of 0.46 g (0.003 mole) 2-amino-4,6-dimethoxypyrimidine in 5 ml methylene chloride was added 1.2 g (0.004 mole) 2-(dimethylaminosulfonyloxy)-benzenesulfonyl isocyanate. The reaction exothermed (18°–26° C.) and was then stirred at room temperature 3 hours. The solvent was evaporated under reduced pressure. The resultant mixture was triturated with diethyl ether and filtered to give 1.2 g of a white solid, m.p. 165°–168° C. The infrared spectrum shows absorption bands at 1710, 1380, 1170 cm$^{-1}$.

Calc. for: C-39.0; H-4.15; N-15.2; S-13.9. Found: C-38.9; H-4.05; N-14.6; S-12.2.

EXAMPLE 3

N-[(4,6-Dimethylpyrimidin-2-yl)aminocarbonyl]-2-(dimethylaminosulfonyloxy)benzenesulfonamide To a suspension of 0.37 g (0.003 mole) 2-amino-4,6-dimethylpyrimidine in 5 ml methylene chloride was added 1.2 g (0.004 mole) 2-(dimethylaminosulfonyloxy)-benzenesulfonyl isocyanate. The reaction exothermed (18°–26° C.) and was stirred at room temperature for 3 hours. The resultant white precipitate was filtered to give 0.9 g of a white solid, m.p. 195°–196° C. The infrared spectrum shows absorption bands at 1705, 1380, 1180 cm$^{-1}$. Calc. for: C-41.9; H-4.46; N-16.3; S-14.9. Found: C-41.9; H-4.50; N-15.5; S-14.9.

EXAMPLE 4

2-(Dimethylaminosulfonyloxy)benzenesulfonamide

To 6.8 g (0.04 mole) 2-hydroxybenzenesulfonamide in 100 ml methylene chloride was added 4.4 g (0.044 mole) triethylamine and 6.3 g (0.044 mole) dimethylsulfamoyl chloride in 5 ml methylene chloride, keeping the reaction temperature <10° C. The mixture was then warmed to room temperature and stirred 72 hours. The reaction mixture was then diluted with 100 ml methylene chloride washed with 100 ml water, 100 ml 1% HCl and dried over MgSO$_4$. The solvent was evaporated to give a crude yellow oil that slowly solidified on standing. The solids were then triturated with hexanes and filtered to give 6.1 g of a tan solid, m.p. 88°–89° C.

Using the procedures similar to those of Examples 1–4, the following compounds can be prepared.

TABLE I

| L | R$_1$ | R$_2$ | R | Q | W | X | Y | Z | m.p. (°C.) |
|---|---|---|---|---|---|---|---|---|---|
| N(CH$_3$)$_2$ | H | H | H | O | O | OCH$_3$ | OCH$_3$ | CH | 165–168 |
| N(CH$_3$)$_2$ | H | H | H | O | O | OCH$_3$ | CH$_3$ | CH | 177–180 |
| N(CH$_3$)$_2$ | H | H | H | O | O | CH$_3$ | CH$_3$ | CH | 195–196 |
| N(CH$_3$)$_2$ | H | H | H | O | O | OCH$_3$ | OCH$_3$ | N | 178–180 |
| N(CH$_3$)$_2$ | H | H | H | O | O | OCH$_3$ | CH$_3$ | N | 191.5–193 |
| N(CH$_3$)$_2$ | H | H | H | O | O | CH$_3$ | CH$_3$ | N | |
| N(CH$_2$)$_2$CH$_3$<br>\|<br>CH$_3$ | H | H | H | O | O | OCH$_3$ | OCH$_3$ | CH | |
| 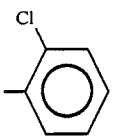 | H | H | H | S | O | OCH$_3$ | CH$_3$ | CH | |
| 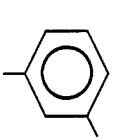 | H | H | H | S | O | OCH$_3$ | CH$_3$ | CH | |
| 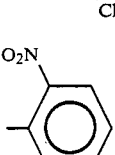 | H | H | H | S | O | OCH$_3$ | CH$_3$ | CH | |
| 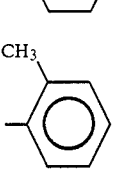 | H | H | H | S | O | OCH$_3$ | CH$_3$ | CH | |
| CH$_3$-phenyl | H | H | H | S | O | OCH$_3$ | CH$_3$ | CH | |

TABLE I-continued

| L | R₁ | R₂ | R | Q | W | X | Y | Z | m.p. (°C.) |
|---|----|----|---|---|---|---|---|---|------------|
| 4-methylphenyl | H | H | H | S | O | CH₃ | CH₃ | CH | |
| CH₂CH₂OCH₃ | H | H | H | S | O | CH₃ | OCH₃ | CH | |
| CH₂CH₂CH₂OCH₃ | H | H | H | S | O | CH₃ | CH₃ | CH | |
| N(CH₂CH₂)₂ (diethylamino) | H | H | H | O | O | CH₃ | CH₃ | CH | |
| pyrrolidin-1-yl | H | H | H | O | O | CH₃ | CH₃ | CH | |
| piperidin-1-yl | H | H | H | O | O | OCH₃ | CH₃ | CH | |
| morpholin-4-yl | H | H | H | O | O | OCH₃ | CH₃ | CH | |
| N(OCH₃)(CH₃) | H | H | H | O | O | OCH₃ | OCH₃ | CH | |
| N(CH₃)₂ | H | H | H | O | O | CH₃ | CH₂CH₂Br | CH | |
| N(CH₃)₂ | H | H | H | O | O | CH₃ | OCH₂CH=CH₂ | CH | |
| N(CH₃)₂ | H | H | H | O | O | CH₃ | OCH₂C(CH₃)=CH₂ | CH | |
| N(CH₃)₂ | H | H | H | O | O | CH₃ | OCH₂C≡CH | CH | |
| N(CH₃)₂ | H | H | H | O | O | CH₃ | OCH₂C≡CCH₃ | CH | |
| N(CH₃)₂ | H | H | H | O | O | CH₃ | OCH₂CH₂OCH₃ | CH | |
| N(CH₃)₂ | H | H | H | O | O | CH₃ | OCH₂CH₂OCH₃ | N | |
| N(CH₃)₂ | H | H | H | O | O | CH₃ | H | CCl | |
| N(CH₃)₂ | H | H | H | O | O | CH₃ | CH₃ | CCH₃ | |
| N(CH₃)₂ | H | H | H | O | O | CH₃ | CH₃ | CCH₂CH₃ | |
| N(CH₃)₂ | H | H | H | N(CH₃) | O | OCH₃ | CH₃ | CH | |
| N(CH₃)₂ | H | H | H | N(CH₃) | O | OCH₃ | OCH₃ | CH | |
| N(CH₃)₂ | H | H | H | N(CH₃) | O | CH₃ | CH₃ | CH | |
| N(CH₃)₂ | H | H | H | N(CH₃) | O | OCH₃ | CH₃ | N | |

TABLE I-continued

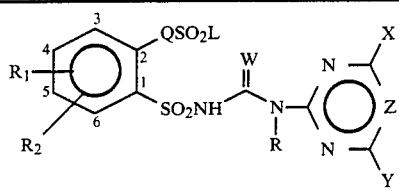

| L | R₁ | R₂ | R | Q | W | X | Y | Z | m.p. (°C.) |
|---|----|----|---|---|---|---|---|---|------------|
| N(CH₃)₂ | H | H | H | N(CH₃) | O | OCH₃ | OCH₃ | N | |
| N(CH₃)₂ | H | H | H | N(CH₃) | O | Cl | OCH₃ | CH | |
| N(CH₃)₂ | H | H | CH₃ | N(CH₃) | O | OCH₃ | OCH₃ | N | |
| N(CH₃)₂ | H | H | CH₃ | N(CH₃) | O | OCH₃ | CH₃ | N | |
| N(CH₃)₂ | H | H | H | O | S | CH₃ | CH₃ | N | |
| NOCH₃(CH₃) | H | H | H | N(CH₃) | O | OCH₃ | OCH₃ | CH | |
| N(CH₃)₂ | H | H | H | N(CH₂)₂CH₃ | O | OCH₃ | OCH₃ | CH | |
| N(CH₃)₂ | H | H | H | S | O | OCH₃ | OCH₃ | CH | |
| N(CH₃)₂ | H | H | H | S | O | CH₃ | CH₃ | CH | |
| N(CH₃)₂ | H | H | H | S | O | OCH₃ | CH₃ | N | |
| N(CH₃)₂ | H | H | H | S | O | OCH₃ | CH₃ | CH | |
| N(CH₃)₂ | H | H | H | S | O | Cl | OCH₃ | CH | |
| N(CH₃)₂ | H | H | H | S | O | OCH₃ | OCH₃ | N | |
| NOCH₃(CH₃) | H | H | H | S | O | OCH₃ | OCH₃ | CH | |
| CH₃ | H | H | H | S | O | CH₃ | CH₃ | CH | |
| CH₂(CH₂)₂CH₃ | H | H | H | S | O | CH₃ | CH₃ | CH | |
| CH₂Cl | H | H | H | S | O | OCH₃ | CH₃ | N | |
| CH₂CF₃ | H | H | H | S | O | OCH₃ | OCH₃ | CH | |
| CH₂(CH₂)₂CH₂Cl | H | H | H | S | O | CH₃ | CH₃ | CH | |
| CH₂Br | H | H | H | S | O | OCH₃ | CH₃ | N | |
| 2-CF₃-C₆H₄ | H | H | H | S | O | OCH₃ | CH₃ | CH | |
| 2-Br-C₆H₄ | H | H | H | S | O | OCH₃ | CH₃ | CH | |
| 2-OCH₃-C₆H₄ | H | H | H | S | O | OCH₃ | CH₃ | CH | |
| 2-F-C₆H₄ | H | H | H | S | O | OCH₃ | CH₃ | CH | |
| N(CH₃)₂ | H | H | H | O | O | OCH₃ | N(CH₃)₂ | N | |
| N(CH₃)₂ | H | H | H | O | O | CH₃ | OCH₂CH₂Br | N | |

TABLE I-continued

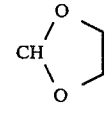

| L | R₁ | R₂ | R | Q | W | X | Y | Z | m.p. (°C.) |
|---|---|---|---|---|---|---|---|---|---|
| N(CH₃)₂ | H | H | H | O | O | CH₃ | OCH₂CH₂F | N | |
| N(CH₃)₂ | H | H | H | O | O | CH₃ | CH₂OCH₂CH₃ | CH | |
| N(CH₃)₂ | H | H | H | O | O | OCH₂CH₃ | OCH₂CH₃ | CH | |
| N(CH₃)₂ | H | H | H | O | O | CH₃ | OCH₂CH₂CH₃ | N | |
| N(CH₃)₂ | H | H | H | O | O | CH₃ | CH(OCH₃)₂ | CH | |
| N(CH₃)₂ | H | H | H | O | O | CH₃ | CH(OCH₂CH₃)₂ | CH | |
| N(CH₃)₂ | H | H | H | O | O | CH₃ | (1,3-dioxolan-2-yl) | CH | |
| N(CH₃)₂ | H | H | H | O | O | CH₃ | CF₃ | CH | |
| N(CH₃)₂ | H | H | H | O | O | CH₃ | OCF₂CHClF | CH | |
| N(Ch₃)₂ | H | H | H | O | O | CH₃ | OCF₂CHBrF | CH | |
| N(CH₃)₂ | H | H | H | O | O | CH₃ | OCF₂CF₂ | CH | |
| N(CH₃)₂ | H | H | H | O | O | CH₃ | OCF₂CHFCF₃ | CH | |
| N(CH₃)₂ | H | H | H | O | O | CH₃ | SCF₂CHClF | CH | |
| N(CH₃)₂ | H | H | H | O | O | CH₃ | SCF₂CHBrF | CH | |
| N(CH₃)₂ | H | H | H | O | O | CH₃ | SCF₂CF₂H | CH | |
| N(CH₃)₂ | H | H | H | O | O | CH₃ | SCF₂CHFCF₃ | CH | |
| N(CH₃)₂ | H | H | H | O | O | Cl | OCH₃ | CH | 155–159° |
| N(CH₃)₂ | H | H | H | O | O | OCF₂H | OCF₂H | CH | |
| N(CH₃)₂ | H | H | H | O | O | Cl | OCF₂H | CH | |
| N(CH₃)₂ | H | H | H | O | O | CH₃ | OCF₂H | CH | |
| N(CH₃)₂ | H | H | H | O | O | OCH₃ | SCF₂H | CH | |
| N(CH₃)₂ | H | H | H | O | O | OCH₃ | OCF₂H | CH | |
| N(CH₃)₂ | H | H | H | O | O | OCH₃ | SCF₂H | N | |
| N(CH₃)₂ | H | H | H | O | O | CH₃ | CH₂CH₃ | CH | |
| N(CH₃)₂ | H | H | H | O | O | OCH₂CH₃ | OCH₂CH₃ | CH | |
| N(CH₃)₂ | H | H | H | O | O | OCH₃ | CF₃ | CH | |
| N(CH₃)₂ | H | H | H | O | O | CH₃ | H | CH | |
| N(CH₃)₂ | H | H | H | O | O | OCH₃ | NH₂ | N | |
| N(CH₃)₂ | H | H | H | O | O | OCH₃ | OCH₂CF₃ | N | |
| N(CH₃)₂ | H | H | H | O | O | OCH₃ | NHCH₃ | N | |
| N(CH₃)₂ | H | H | CH₃ | O | O | OCH₃ | OCH₃ | CH | |
| N(CH₃)₂ | H | H | CH₃ | O | O | OCH₃ | CH₃ | CH | |
| N(CH₃)₂ | H | H | CH₃ | O | O | OCH₃ | OCH₃ | N | |
| N(CH₃)₂ | H | H | CH₃ | O | O | OCH₃ | CH₃ | N | |
| N(CH₃)₂ | 5-Cl | H | H | O | O | OCH₃ | OCH₃ | CH | |
| N(CH₃)₂ | 5-Cl | H | H | O | O | OCH₃ | CH₃ | CH | |
| N(CH₃)₂ | 5-Cl | H | H | O | O | OCH₃ | CH₃ | N | |
| N(CH₃)₂ | 5-Cl | H | H | O | O | OCH₃ | OCH₃ | N | |
| N(CH₃)₂ | 5-Cl | H | H | O | O | Cl | OCH₃ | CH | |
| N(CH₃)₂ | 5-CH₃ | H | H | O | O | OCH₃ | OCH₃ | CH | |
| N(CH₃)₂ | 5-CH₃ | H | H | O | O | OCH₃ | CH₃ | CH | |
| N(CH₃)₂ | 5-CH₃ | H | H | O | O | CH₃ | CH₃ | CH | |
| N(CH₃)₂ | 5-CH₃ | H | H | O | O | OCH₃ | CH₃ | N | |
| N(CH₃)₂ | 5-CH₃ | H | H | O | O | OCH₃ | OCH₃ | N | |
| N(CH₃)₂ | 5-CH₃ | H | H | O | O | Cl | OCH₃ | CH | |
| N(CH₃)₂ | 6-CH₃ | H | H | O | O | OCH₃ | OCH₃ | CH | |
| N(CH₃)₂ | 6-CH₃ | H | H | O | O | OCH₃ | CH₃ | CH | |
| N(CH₃)₂ | 6-CH₃ | H | H | O | O | CH₃ | CH₃ | CH | |
| N(CH₃)₂ | 6-CH₃ | H | H | O | O | OCH₃ | CH₃ | N | |
| N(CH₃)₂ | 6-CH₃ | H | H | O | O | OCH₃ | OCH₃ | N | |
| N(CH₃)₂ | 6-CH₃ | H | H | O | O | Cl | OCH₃ | CH | |
| N(CH₃)₂ | 5-F | H | H | O | O | CH₃ | CH₃ | CH | |
| N(CH₃)₂ | 5-Br | H | H | O | O | CH₃ | CH₃ | CH | |
| N(CH₃)₂ | 3-Cl | H | H | O | O | CH₃ | CH₃ | CH | |
| N(CH₃)₂ | 3-Cl | 5-Cl | H | O | O | CH₃ | CH₃ | CH | |
| N(CH₃)₂ | 5-OCH₃ | H | H | O | O | CH₃ | CH₃ | CH | |
| N(CH₃)₂ | 5-CF₃ | H | H | O | O | CH₃ | CH₃ | CH | |
| N(CH₃)₂ | 5-NO₂ | H | H | O | O | CH₃ | CH₃ | CH | |
| N(CH₃)₂ | H | H | H | O | O | OCH₃ | —(CH₂)₃CH₃ | CH | |
| N(CH₃)₂ | H | H | H | O | O | CH₃ | —OCH₂CF₃ | N | |
| N(CH₃)₂ | H | H | H | O | O | CH₃ | —OCH₂CCl₃ | N | |
| N(CH₃)₂ | H | H | H | O | O | CH₃ | —OCH₂CBr₃ | N | |
| N(CH₃)₂ | H | H | H | O | O | CH₃ | OCH₂CH₂Cl | N | |
| N(CH₃)₂ | H | H | H | O | O | CH₃ | —CH₂CH₂Cl | CH | |
| N(CH₃)₂ | H | H | H | O | O | CH₃ | —O(CH₂)₃CH₃ | N | |

TABLE I-continued

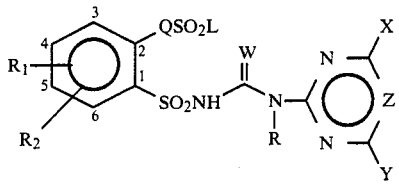

| L | R₁ | R₂ | R | Q | W | X | Y | Z | m.p. (°C.) |
|---|---|---|---|---|---|---|---|---|---|
| N(CH₃)₂ | H | H | H | O | O | CH₃ | —OCH₂CH=CH₂ | N | |
| N(CH₃)₂ | H | H | H | O | O | CH₃ | —OCH₂C=CH₂ \| CH₃ | N | |
| N(CH₃)₂ | H | H | H | O | O | CH₃ | OCH₂C≡CH | N | |
| N(CH₃)₂ | H | H | H | O | O | CH₃ | OCH₂C≡CCH₃ | N | |
| N(CH₃)₂ | H | H | H | O | O | CH₃ | —CH₂OCH₃ | CH | |
| N(CH₃)₂ | H | H | H | O | O | CH₃ | SCH₃ | CH | |
| N(CH₃)₂ | H | H | H | O | O | CH₃ | SCH₂CH₃ | CH | |
| N(CH₃)₂ | H | H | H | O | O | CH₃ | CH₃ | CBr | |
| N(CH₃)₂ | H | H | H | O | O | CH₃ | CH₃ | CF | |
| N(CH₃)₂ | H | H | H | O | O | CH₃ | CH₃ | CCl | |

TABLE II

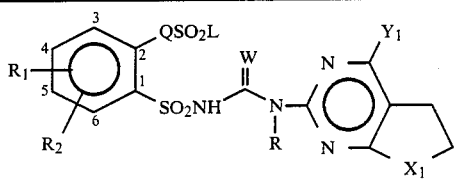

| L | R₁ | R₂ | R | Q | W | X₁ | Y₁ | m.p. (°C.) |
|---|---|---|---|---|---|---|---|---|
| N(CH₃)₂ | H | H | H | O | O | O | H | |
| N(CH₃)₂ | H | H | H | O | O | O | CH₃ | |
| N(CH₃)₂ | H | H | H | O | O | O | OCH₃ | |
| N(CH₃)₂ | H | H | H | O | O | O | Cl | |
| N(CH₃)₂ | H | H | H | O | O | CH₂ | H | |
| N(CH₃)₂ | H | H | H | O | O | CH₂ | CH₃ | |
| N(CH₃)₂ | H | H | H | O | O | CH₂ | OCH₃ | |
| N(CH₃)₂ | H | H | H | O | O | CH₂ | Cl | |
| N(CH₃)₂ | 5-Cl | H | H | O | O | O | CH₃ | |
| N(CH₃)₂ | 5-Cl | H | H | O | O | O | OCH₃ | |
| N(CH₃)₂ | 5-CH₃ | H | H | O | O | O | CH₃ | |
| N(CH₃)₂ | 5-CH₃ | H | H | O | O | O | OCH₃ | |
| N(CH₃)₂ | 6-CH₃ | H | H | O | O | O | CH₃ | |
| N(CH₃)₂ | 6-CH₃ | H | H | O | O | O | OCH₃ | |
| NOCH₃ \| CH₃ | H | H | H | O | O | O | CH₃ | |
| NOCH₃ \| CH₃ | H | H | H | O | O | O | OCH₃ | |
| NOCH₃ \| CH₃ | H | H | H | O | O | O | Cl | |
| NOCH₃ \| CH₃ | H | H | H | O | O | CH₂ | CH₃ | |
| NOCH₃ \| CH₃ | H | H | H | O | O | CH₂ | OCH₃ | |
| NOCH₃ \| CH₃ | H | H | H | O | O | CH₂ | Cl | |
| CH₃ | H | H | H | S | O | O | CH₃ | |

TABLE III

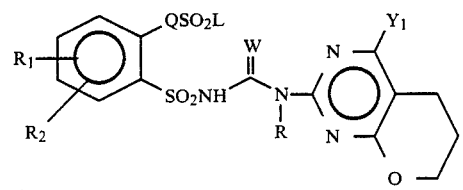

| L | R₁ | R₂ | R | Q | W | Y₁ | m.p. (°C.) |
|---|---|---|---|---|---|---|---|
| N(CH₃)₂ | H | H | H | O | O | H | |
| N(CH₃)₂ | H | H | H | O | O | CH₃ | |
| N(CH₃)₂ | H | H | H | O | O | OCH₃ | |
| N(CH₃)₂ | H | H | H | O | O | Cl | |
| N(CH₃)₂ | 5-Cl | H | H | O | O | OCH₃ | |
| N(CH₃)₂ | 5-CH₃ | H | H | O | O | OCH₃ | |
| N(CH₃)₂ | 6-CH₃ | H | H | O | O | OCH₃ | |
| NOCH₃ \| CH₃ | H | H | H | O | O | CH₃ | |
| NOCH₃ \| CH₃ | H | H | H | O | O | OCH₃ | |
| NOCH₃ \| CH₃ | H | H | H | O | O | Cl | |
| NOCH₃ \| CH₃ | H | H | H | O | O | H | |

TABLE IV

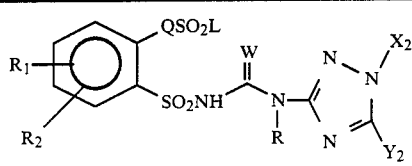

| L | R₁ | R₂ | R | Q | W | X₂ | Y₂ | m.p. (°C.) |
|---|---|---|---|---|---|---|---|---|
| N(CH₃)₂ | H | H | H | O | O | CH₃ | CH₃ | |
| N(CH₃)₂ | H | H | H | O | O | CH₃ | OCH₃ | |
| N(CH₃)₂ | H | H | H | O | O | CH₃ | SCH₃ | |
| N(CH₃)₂ | H | H | H | O | O | CH₂CH₃ | CH₃ | |

TABLE IV-continued

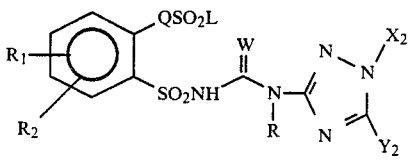

| L | R₁ | R₂ | R | Q | W | X₂ | Y₂ | m.p. (°C.) |
|---|----|----|---|---|---|-----|-----|-----------|
| N(CH₃)₂ | H | H | H | O | O | CH₂CF₃ | CH₃ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, can contain from about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE V

|  | Active* Ingredient | Inert Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973 pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 5

Wettable Powder

| | |
|---|---|
| N—[(4,6-dimethoxy-1,3,5-triazin-2-yl)aminocarbonyl]-2-(dimethylaminosulfonyloxy)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 6

Wettable Powder

| | |
|---|---|
| N—[(4,6-dimethoxypyrimidin-2-yl)aminocarbonyl]-2-(dimethylaminosulfonyloxy)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 7

Granule

| | |
|---|---|
| Wettable Powder of Example 6 | 5% |
| attapulgite granules (U.S.S. 20–40 mesh: 0.84–0.42 mm) | 95% |

A slurry of wettable powder containing ≈25% solids is sprayed on the surface of attapulgite granules in a double-cone blender. The granules are dried and packaged.

EXAMPLE 8

Extruded Pellet

| | |
|---|---|
| N—[(4-chloro-6-methoxypyrimidin-2-yl)aminocarbonyl]-2-(dimethylaminosulfonyloxy)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 9

Oil Suspension

| | |
|---|---|
| N—[(4,6-dimethoxypyrimidin-2-yl)aminocarbonyl]-2-(dimethylaminosulfonyloxy)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 10

Wettable Powder

| | |
|---|---|
| N—[(4-chloro-6-methoxypyrimidin-2-yl)aminocarbonyl]-2-(dimethylaminosulfonyloxy)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 11

Low Strength Granule

| | |
|---|---|
| N—[(4,6-dimethoxypyrimidin-2-yl)aminocarbonyl]-2-(dimethylaminosulfonyloxy)benzenesulfonamide | 1% |
| N,N—dimethylformamide | 9% |
| attapulgite granules (U.S.S 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged

EXAMPLE 12

Aqueous Suspension

| | |
|---|---|
| N—[(4,6-dimethylpyrimidin-2-yl)aminocarbonyl]-2-(dimethylaminosulfonyloxy)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 13

Solution

| | |
|---|---|
| N—[(4-methyl-6-methoxy-1,3,5-triazin-2-yl)aminocarbonyl]-2-(dimethylaminosulfonyloxy)benzenesulfonamide | 5% |
| water | 95% |

The salt is added directly to the water with stirring to produce the solution, which may then be packaged for use.

EXAMPLE 14

Low Strength Granule

| | |
|---|---|
| N—[(4-chloro-6-methoxypyrimidin-2-yl)aminocarbonyl]-2-(dimethylaminosulfonyloxy)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 15

Granule

| | |
|---|---|
| N—[(4-methyl-6-methoxypyrimidin-2-yl)aminocarbonyl]-2-(dimethylaminosulfonyloxy)benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 16

High Strength Concentrate

| | |
|---|---|
| N—[(4,6-dimethylpyrimidin-2-yl)aminocarbonyl]-2-(dimethylaminosulfonyloxy)benzenesulfonamide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 17

Wettable Powder

| | |
|---|---|
| N—[(4-methyl-6-methoxy-1,3,5-triazin-2-yl)aminocarbonyl]-2-(dimethylaminosulfonyloxy)benzenesulfonamide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 18

Wettable Powder

| | |
|---|---|
| N—[(4-methyl-6-methoxypyrimidin-2-yl)aminocarbonyl]-2-(dimethylaminosulfonyloxy)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 19

Oil Suspension

| | |
|---|---|
| N—[(4,6-dimethoxy-1,3,5-triazin-2-yl)aminocarbonyl]-2-(dimethylaminosulfonyloxy)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention and their agriculturally suitable salts are useful for broad-spectrum pre- and/or post-emergence weed control in areas where complete control of all vegetation is desired, such as around fuel storage tanks, ammunition depots, industrial storage areas, parking lots, drive-in theaters, around billboards and railroad structures, and along highways. In addition, the subject compounds can be used for selective pre- or post-emergence weed control in cereal crops, such as wheat.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results are described below.

TEST A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (Xanthium sp.), sorghum, corn, soybean, sugar beet, rice, wheat, cotton and purple nutsedge (*Cyperus rotundus*) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effect; and
U=unusual pigmentation.

The data indicate that the compounds tested have utility for pre- and/or post-emergence weed control in wheat. In addition, at higher rates of application the compounds should be useful for industrial weed control.

Compounds

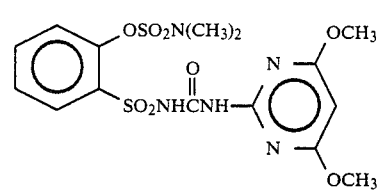

Compound 1

-continued
Compounds

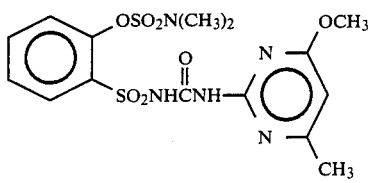

Compound 2

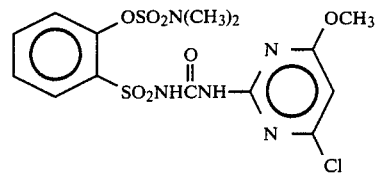

Compound 6

TABLE A

| | Compound 1 | | Cmpd. 2 | Cmpd. 3 | Cmpd. 4 | Cmpd. 5 | Cmpd. 6 |
|---|---|---|---|---|---|---|---|
| grams/ha | 50 | 400 | 50 | 50 | 50 | 50 | 50 |
| POST-EMERGENCE | | | | | | | |
| Cotton | 9C | 9C | 9C | 9C | 9C | 9C | 9C |
| Morningglory | 10C | 10C | 9C | 5C,9G | 9C | 9C | 9C |
| Cocklebur | 9C | 9C | 5C,9G | 5C,9G | 4C,9G | 5C,9H | 4C,9H |
| Sicklepod | 9C | 9C | 4C,9G | 2C,7H | 4C,9H | 5C,9G | 3C,8G |
| Nutsedge | 5C,9G | 5C,9G | 9G | 5G | 3G | 2G | 3C,9G |
| Crabgrass | 4C,9G | 5C,9G | 3C,9G | 5G | 2C,4G | 1C,3G | 1C,3G |
| Barnyardgrass | 9C | 9C | 2C,9H | 2C,6H | 2C,8H | 7H | 3C,9H |
| Wild Oats | 2C,8G | 2C,9G | 5G | 6G | 3G | 0 | 0 |
| Wheat | 0 | 3G | 0 | 0 | 0 | 0 | 0 |
| Corn | 1U,9G | 4C,9G | 3C,9H | 1C,4G | 2C,9H | 3C,8H | 2C,6H |
| Soybean | 9C | 9C | 9C | 4C,6G | 4C,9G | 9C | 4C,7H |
| Rice | 5C,9G | 5C,9G | 5C,9G | 4C,8G | 3C,5G | 5C,6G | 4C,6G |
| Sorghum | 4C,9G | 4C,9G | 5C,9H | 5C,9H | 4C,9H | 3C,9H | 9H |
| Sugar beet | 9C | 9C | 5C,9G | 4C,9G | 5C,9G | 9C | 4C,9G |
| PRE-EMERGENCE | | | | | | | |
| Morningglory | 9G | 9C | 9C | 9H | 9G | 9C | 9C |
| Cocklebur | 9H | 9H | 9H | 9H | 9H | 9H | 9H |
| Sicklepod | 9G | 9G | 9G | 4G | 9G | 9G | 2C,2H |
| Nutsedge | 10E | 10E | 10E | 9G | 2C | 5G | 10E |
| Crabgrass | 5C,9G | 5C,9G | 2C,6G | 2G | 2G | 4G | 2G |
| Barnyardgrass | 9H | 9H | 5C,9H | 2C,3G | 3C,5G | 4C,7G | 3C,8H |
| Wild Oats | 3C,7G | 2C,8H | 3C,8G | 2C,5G | 2C,4G | 4G | 4G |
| Wheat | 0 | 5G | 6G | 0 | 0 | 0 | 1C |
| Corn | 5C,9H | 9H | 3C,9H | 2U,7G | 3C,9H | 4C,9H | 2C,8G |
| Soybean | 9H | 9H | 9H | 2C,2H | 4C,6H | 4C,6H | 2C,2H |
| Rice | 10E | 10E | 3C,9H | 5C,9H | 2C,8G | 4C,8G | 4C,9H |
| Sorghum | 5C,9H | 5C,9H | 3C,9H | 5C,9H | 5C,9H | 5C,9H | 5C,9H |
| Sugar beet | 9C | 10E | 10C | 5C,9G | 10E | 5C,9G | 5C,9G |
| Cotton | 9C | 9G | 4C,9G | 9G | 3C,9G | 3C,9G | 5C,9G |

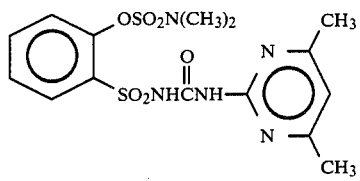

Compound 3

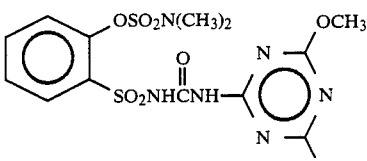

Compound 4

Compound 5

What is claimed is:
1. A compound of the formula:

$$\text{R}_1 - \text{C}_6\text{H}_3(\text{OSO}_2\text{L})(\text{SO}_2\text{NHC}(\text{W})\text{N}(\text{R})\text{-A})$$

wherein
W is O or S;
R is H or CH$_3$;
Q is O, or NR$_3$;
L is NR$_5$R$_6$ or N(OCH$_3$)CH$_3$;
R$_1$ is H, F, Cl, Br, CH$_3$, OCH$_3$, CF$_3$ or NO$_2$;
R$_2$ is H or Cl;
R$_3$ is H or C$_1$-C$_3$ alkyl;
R$_5$ and R$_6$ are independently C$_1$-C$_3$ alkyl, or R$_5$ and R$_6$ may be taken together to be —(CH$_2$)$_4$—, —(CH$_2$)$_5$— or —(CH$_2$)$_2$O(CH$_2$)$_2$—;
A is

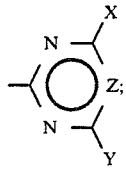     A-1

X is $CH_3$, $OCH_3$, $CH_2CH_3$, $OCH_2CH_3$ or $OCF_2H$;
Y is H, $NH_2$, $NHCH_3$, $N(CH_3)_2$, $C_1$-$C_4$ alkyl, $C_1$-$C_4$ alkyl substituted with 1–3 atoms of (a) F, (b) Cl or (c) Br, $CH_2OCH_3$, $CH_2OCH_2CH_3$, $C_1$-$C_4$ alkoxy, $C_1$-$C_2$ alkylthio, $C_3$-$C_4$ alkenyloxy, $C_3$-$C_4$ alkynyloxy, $OCH_2CH_2OCH_3$, $CH(OCH_3)_2$, $CH(OCH_2CH_3)_2$,

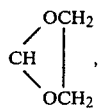

$OCH_2CF_3$, $OCH_2CH_2F$, $OCH_2CH_2Cl$, $OCH_2CH_2Br$ or $GCF_2T$ wherein G is O or S and T is H, CHClF, CHBrF, $CF_2H$ or $CHFCF_3$;
Z is N;
provided that
when W is S, then R is H;
and their agriculturally suitable salts.

2. Compounds of claim 1 where W is O.
3. Compounds of claim 2 where $R_2$ is H.
4. Compounds of claim 3 where $R_3$ is $CH_3$, $R_5$ is $CH_3$ and $R_6$ is $CH_3$ or $CH_2CH_3$.
5. Compounds of claim 4 where Q is O and $R_1$ is H, $CH_3$ or Cl.
6. Compounds of claim 5 where X is $CH_3$, $OCH_3$, Cl or $OCF_2H$ and Y is $CH_3$, $CH_2CH_3$, $OCH_3$, $OCH_2CH_3$, $OCF_2H$, $SCF_2H$, $CH_2OCH_3$ or $CF_3$.
7. Compounds of claim 6 where R is H and $R_1$ is H.
8. The compound of claim 1 which is N-[(4-methyl-6-methoxy-1,3,5-triazin-2-yl)aminocarbonyl]-2-dimethylaminosulfonyloxy)benzenesulfonamide.
9. The compound of claim 1 which is N-[(4,6-dimethoxy-1,3,5-triazin-2-yl)aminocarbonyl]-2-(dimethylaminosulfonyloxy)benzenesulfonamide.
10. A composition suitable for controlling the growth of undesired vegetation which comprises an effective amount of a compound of claim 1 and at least one of the following: surfactant, solid or liquid diluent.
11. A composition suitable for controlling the growth of undesired vegetation which comprises an effective amount of a compound of claim 4 and at least one of the following: surfactant, solid or liquid diluent.
12. A composition suitable for controlling the growth of undesired vegetation which comprises an effective amount of a compound of claim 5 and at least one of the following: surfactant, solid or liquid diluent.
13. A composition suitable for controlling the growth of undesired vegetation which comprises an effective amount of a compound of claim 6 and at least one of the following: surfactant, solid or liquid diluent.
14. A method for controlling the growth of undesired vegetation which comprises applying to the locus to be protected an effective amount of a compound of claim 1.
15. A method for controlling the growth of undesired vegetation which comprises applying to the locus to be protected an effective amount of a compound of claim 4.
16. A method for controlling the growth of undesired vegetation which comprises applying to the locus to be protected an effective amount of a compound of claim 5.
17. A method for controlling the growth of undesired vegetation which comprises applying to the locus to be protected an effective amount of a compound of claim 6.

* * * * *

UNITED STATES PATENT OFFICE
CERTIFICATE OF CORRECTION

PATENT NO. : 4,576,633
DATED : March 18, 1986
INVENTOR(S) : James J. Reap

It is certified that error appears in the above-identified patent and that said Letters Patent are hereby corrected as shown below:

Column 26, lines 50 to 55

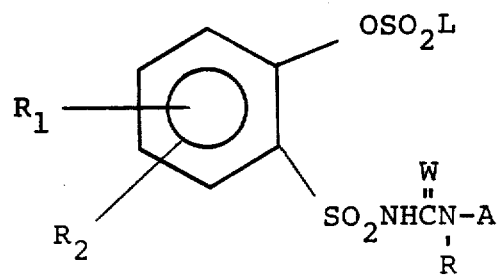

UNITED STATES PATENT AND TRADEMARK OFFICE
CERTIFICATE OF CORRECTION

PATENT NO. : 4,576,633
DATED : March 18, 1986
INVENTOR(S) : James J. Reap

It is certified that error appears in the above-identified patent and that said Letters Patent is hereby corrected as shown below:

should read as follows:

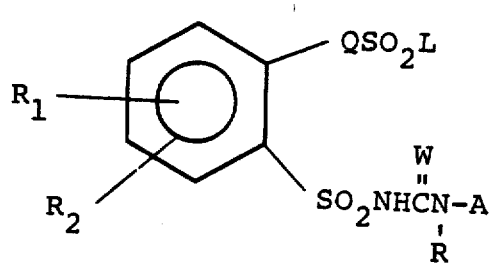

Signed and Sealed this

Eighth Day of September, 1987

Attest:

DONALD J. QUIGG

Attesting Officer

Commissioner of Patents and Trademarks